(12) United States Patent
Stewart et al.

(10) Patent No.: US 6,383,150 B1
(45) Date of Patent: May 7, 2002

(54) NETWORK-BASED SYSTEM FOR DIAGNOSING BALANCE DISORDERS

(75) Inventors: Kendal L. Stewart, Cedar Park; Bridgett D. Wallace, Austin, both of TX (US)

(73) Assignee: Vestent, L.P., Austin, TX (US)

( * ) Notice: Subject to any disclaimer, the term of this patent is extended or adjusted under 35 U.S.C. 154(b) by 0 days.

(21) Appl. No.: 09/897,589

(22) Filed: Jul. 2, 2001

(51) Int. Cl.[7] .................................................. A61B 5/00
(52) U.S. Cl. ...................................... 600/595; 600/300
(58) Field of Search ................................ 600/300, 587, 600/595

(56) References Cited

U.S. PATENT DOCUMENTS

| | | | |
|---|---|---|---|
| 5,269,318 A | 12/1993 | Nashner | 128/782 |
| 5,303,715 A | 4/1994 | Nashner et al. | 128/782 |
| 5,551,445 A | 9/1996 | Nashner | 128/782 |
| 5,980,429 A | 11/1999 | Nashner | 482/8 |
| 6,063,046 A | * 5/2000 | Allum | 600/595 |

* cited by examiner

Primary Examiner—Max Hindenburg
(74) Attorney, Agent, or Firm—Gunn, Lee & Hanor, P.C.; Charles W. Hanor; Ted D. Lee

(57) ABSTRACT

A test administration center is provided at which a plurality of balance diagnostic tests are administered on a patient. A test evaluation center, located remotely from the test administration center, is provided at which diagnostic data is evaluated by a skilled clinician. A computer network links, and transfers data from, the test administration center to both the test evaluation center, where the data is evaluated, and to a patient database, where the data is stored.

34 Claims, 2 Drawing Sheets

NETWORK-BASED SYSTEM FOR DIAGNOSING BALANCE DISORDERS

FIELD OF THE INVENTION

The invention relates to the diagnosis of balance disorders, and particularly to a network-based system for remotely evaluating balance-related diagnostic test data.

BACKGROUND

The brain maintains a sense of spatial orientation and equilibrium by integrating and interpreting a variety of different sensory inputs from the visual, vestibular (inner ear), and somatosensory (muscles, skin, and joints) systems. The most complex source of spatial cues is the vestibular system of the inner ear. Indeed, studies have shown that the vast majority of patients complaining of dizziness have a vestibular abnormality.

The inner ear has two types of spatial orientation sensors. Three endolymphatic-fluid-filled semi-circular canals provide sensory information about velocity, rotation, and angular motion. Two otolith organs in each inner ear, the utricle and the saccule, sense horizontal and vertical acceleration, respectively. Specialized hair cells in the otoliths and the ampullae (the dilated portions of the semi-circular canals) are displaced by movement in one direction or the other. These displacements are converted in neural signals, which are transmitted by the vestibular nerve to the brain. When the head is in a normal upright position, the hair cells in each ear fire equally at a static rate. When the head tilts to the right or to the left, the hair cells in each ear fire at different rates. The central nervous system recognizes the difference in the firing rate to determine where the head is in space.

The sensory data from the inner ear is complemented by visual cues from the eyes and somatosensory spatial cues from the muscles and skin, which sense pressure and muscle tensioning caused by standing, sitting, or lying down.

Sensory mismatch occurs when the various sensory inputs of the body do not agree with one another. For example, a room on a ship in a stormy sea may look upright at the same time the gravity sensors in the inner ear and pressure sensors in the feet indicate that the room is tilted at an angle. Sensory mismatch can result in nausea, queaziness, and disorientation.

Several different conditions can cause the balance system to malfunction. Labyrinthitis and Vestibular Neuronitis are conditions that describe the inflammation of the inner ear or the vestibular nerve, typically caused by a viral infection. These conditions are characterized by a sudden onset of vertigo which is "spinning" in nature, extreme nausea, and vomiting.

Endolymphatic Hydrops is a condition of the inner ear related to the inability of the ear to regulate its fluid balance, resulting in an episodic buildup of pressure within the balance and hearing organs. This disorder is characterized by spontaneous episodes of vertigo lasting up to several hours, fullness of the ear, "ringing" or noise in the ear, and/or hearing loss. When all of these symptoms are present, the disorder is described as Meniere's Disease. Endolymphatic Hydrops has many causes, including Labyrinthitis, perilymphatic fistula, concussions, noise trauma, autoimmune inner ear disease, and ear surgery. This disorder is thought to be related to herpetic group viruses. Immune stimulation from allergies, stress, illness or hormonal changes tend to worsen these symptoms.

Benign Paroxysmal Positional Spinning (BPPV) is a condition characterized by the positional onset of vertigo. Brief episodes of vertigo may be caused by lying down, rolling over in bed, or tilting the head back to look up. Canalithiasis, a form of BPPV associated with vertigo lasting only a few seconds, is thought to be caused by misplaced calcium carbonate crystals (otoconia) that have been dislodged from the inner ear and which float freely within the semi-circular canals in response to gravity. Cupulolithiasis, a form of BPPV associated with vertigo lasting several minutes, is caused by misplaced otoconia stuck to the cupula that constantly stimulate the balance sensor.

Perilymphatic fistula is caused by a hole in the inner ear that leaks endolymphatic fluid into the middle ear. Leakage results in brief episodes of vertigo triggered by rapid changes in middle ear pressure, such as that caused by coughing, sneezing, lifting, scuba diving, head trauma, or rapid changes in altitude.

Vertebribasular Insufficiency (VBI) is a common vascular disorder characterized by decreased blood flow through the vertebrobasilar artery system, which can result in an abrupt onset of vertigo that resolves after several minutes of lying down. Such episodes are accompanied by other VBI symptoms, including visual hallucinations, drop attacks, visual field deficits, diplopia, and headache.

Otoxicity is a condition characterized by damage done to the hearing and balance systems by drugs. Common medications that can permanently damage the inner ear system include Aminoglycoside antibiotics and Cisplatin. Symptoms may include gait unsteadiness, imbalance, and oscillopsia (a bouncing sensation of the horizon).

Other disorders are characterized by gravity sensors in the otolith organs being excessively responsive to internal pressure changes such as that caused by physical activity and sound. Damage can also be caused by tumors and viral infections that affect the vestibular nerve.

Vestibular abnormalities cause not only the common symptoms of dizziness, spinning, unsteadiness, and nausea, but also cognitive dysfunction, including short-term memory deficits, inability to concentrate or focus on a task, panic attacks, and depression. These cognitive symptoms are caused by the brain's natural compensation mechanisms. To suppress the sensory input from the malfunctioning ear, the brain decreases the relative function of the brain's reticular activating system (the portion of the brain responsible for "awareness" or the feeling of being "awake" or "clear") which secondarily increases the activity of the limbic system (the portion of the brain responsible for moods and emotions).

Approximately 12.5 million physician's office visits per year, or five to ten percent of all office visits, are for the complaint of dizziness. A National Institutes of Health study estimates that forty percent of the population over the age of forty have experienced or will experience a "dizziness" disorder during their lifetime. But dizziness affects the young as well. Each year over 450,000 people, mostly young adults, suffer concussions or mild head injuries. Of those requiring short-term hospitalization, a large majority complain of persistent symptoms of dizziness or memory loss.

Unfortunately, many sufferers of dizziness or vertigo disorders do not receive proper diagnosis or therapy. Because the symptoms are vague, and the possible causes multitudinous, sufferers are often improperly diagnosed. Worse, sufferers are often treated as "problem patients" or inappropriately referred to psychiatrists and neurologists.

Athletes in contact and high-impact sports experience a high incidence of vestibular abnormalities caused by mild to severe head injuries. Unfortunately, athletes in professional and even college sports are seldom adequately diagnosed for vestibular abnormalities following a jarring collision, blow to the head, or other minor injury before being sent back onto the playing field.

There are a variety of tests for diagnosing balance disorders of the vestibular system. One test is a hearing test. Balance disorders are often accompanied by problems with hearing especially hearing of low frequencies. Another test is a posturography test, in which a person stands on a moving platform and the movement of the ankles and hips are measured. Posturography tests the vestibular-spinal reflex, which is manifested in the movements various body muscles make to maintain postural balance and coordination. Posturography is useful for detecting disorders in the otolith organs of the ear, because both the somasensatory system and the otoliths detect acceleration (including gravity).

The Vestibular Autorotational Test (VAT®) evaluates the function of the vestibulo-ocular reflex (VOR) by measuring how quickly and accurately our eyes move to compensate for head movement. The VOR allows us to have clear vision during movement. For example, when a person turns his head 30 degrees to the right, the eyes should simultaneously turn 30 degrees to the left. If the eyes turn too little or turn too much, it suggests that the vestibular system may be damaged. The vestibular ocular reflex test is useful in detecting disorders originating in, or affecting, the semicircular canals of the ear. Sensory input from the semicircular canals allows the brain to generate eye movements that match the velocity of the head movement.

Despite the existence of various balance dysfunction tests and many methods of treatment, balance disorder treatment is underutilized by the public at large.

BRIEF SUMMARY OF THE INVENTION

Various aspects of the present invention address at least some of the needs of the prior art. In one aspect, the present invention provides a system for diagnosing balance function comprising a test administration center at which a plurality of balance diagnostic tests are administered on a patient, and a remote test evaluation center at which said diagnostic data is evaluated by a skilled clinician, leading to a diagnosis of said patient. A computer network links, and transfers data from, the test administration center to both the test evaluation center, where the data is evaluated, and to a patient database, where the data is stored.

In another aspect, the present invention provides a process for diagnosing the balance system of a patient, the process comprising the steps of a primary care physician of the patient referring the patient to the balance disorder diagnostic provider, the patient registering with the provider and completing a questionnaire for the provider; the provider obtaining authorization from an insurance carrier of the patient to administer the diagnostic balance tests; the patient scheduling an appointment for a plurality of diagnostic balance tests; an affiliate of the provider administering, at the appointed time, the plurality of diagnostic balance tests on the patient using diagnostic testing machines that generate diagnostic data, said plurality of diagnostic balance tests being administered at a first location; a network transmitting the diagnostic data from said diagnostic testing machines to a patient database that stores said diagnostic data; the provider retrieving, at a second location distinct and independent from the first location, the diagnostic data from said patient database; the provider evaluating the diagnostic data to diagnose the patient; the provider recommending therapy to improve the patient's vestibular functioning; the provider forwarding the diagnosis and recommended therapy to the primary care physician; and the primary care physician referring the patient to the clinic for therapy.

A further aspect of the present invention provides widespread access to state-of-the-art diagnostic modalities. Another aspect of the present invention provides off-site "expert" interpretation of balance dysfunction test data and expert guidance through a global network. Yet another aspect of the present invention provides a platform that integrates a plurality of diagnostic tools, transfers the associated data to a database on the global network, and provides for off-site diagnosis and customization of therapy. Further aspects of the present invention link a regional balance center, a satellite balance testing center, the primary care physician, the patient, and a database through a global computer network. Another aspect of the present invention centrally stores clinical and diagnostic information.

One of the advantages of the present invention is that it gives patients, healthcare providers, athletes, coaches, physical trainers, and others a more complete picture of how well the vestibular system is interacting with the body and brain. Another advantage is that it aids in accurate evaluation and treatment of the specific sensory abnormality by assisting the healthcare provider in distinguishing the source of the symptoms. A further advantage of the present information is that it promotes a team approach to working with patients and athletes, by coordinating athletic trainers with physicians and therapists.

A further advantage of the system and procedure of the present invention is that it provides cost-effective screening, diagnosis, and customized therapeutics for patients with vestibular based disorders. A yet further advantage is that a person seeking treatment can apply and set up an appointment for treatment from any personal computer linked to the global network.

Another advantage of the system and procedure of the present invention is that it facilitates early and aggressive vestibular therapy to minimize and compensate vestibular abnormalities. Administered early after a concussion or mild head injury, aggressive vestibular therapy helps the brain to learn to compensate for vestibular abnormalities without suppressing secondary cerebral functions. Even administered long after an injury, the present invention helps identify the abnormalities and allow customized therapy to restore cognitive abilities to normal performance.

Another advantage of the system and procedure of the present invention is enhancement of athletic performance. Even minor, subtle vestibular abnormalities, which might be tolerable to an ordinary individual performing ordinary tasks, can impair athletic performance and physical coordination, increasing the risk of further injury. Treatments of athletes in accordance with one aspect of the present invention enhances the vestibulo-ocular reflex (VOR), increasing the athlete's clarity of vision during rapid eye movement.

The benefits of the present invention redound not only to athletes and concussion sufferers, but also to the elderly and the public at large. Every year, one-third to one-half of the population over age 65 experiences falls, many of which lead to orthopedic injuries, including disabling hip fractures. Many of these falls are due to, or contributed by, underlying inner ear disorders. The present invention's system and procedure for routine and early detection of balance abnormalities significantly reduces the risk of falling for elderly patients.

Moreover, recent clinical experience suggests that some common processing disorders, such as attention deficit disorder, attention deficit hyperactivity disorder, learning disorder, central auditory processing disorder, and visual processing disorder, may merely be symptoms of an underlying inner ear abnormality. Therapeutic regimens administered in accordance with the present invention will improve, if not completely reverse, such central processing disorders.

Other aspects and advantages of the present invention will be more clearly understood after reference to the following detailed description read in conjunction with the drawings.

DETAILED DESCRIPTION

Figure 1:
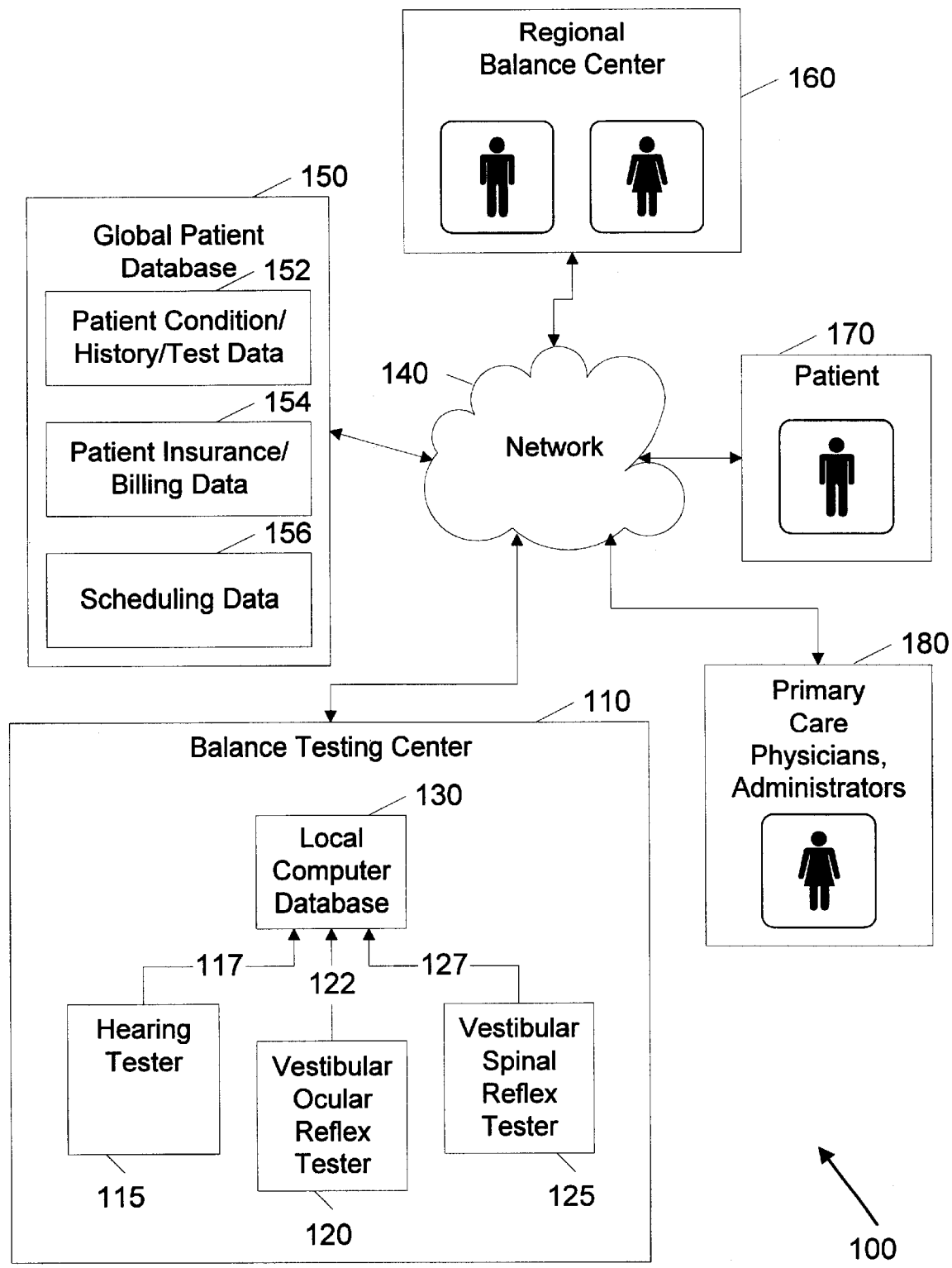
FIG. 1 is a block diagram of one embodiment of a system for remotely diagnosing balance disorders, built in accordance with the present invention.

FIG. 1 is a block diagram of one embodiment of a system 100 for diagnosing balance disorders via a network. The exemplary embodiment provides a regional balance center 160 that is linked via a network 140 to a satellite balance testing center 110. The regional balance center 160 is staffed with physicians and clinicians expert at interpreting balance diagnostic data and developing therapeutic regimens to treat balance disorders. The satellite balance testing center 110 is typically an outpatient rehabilitation center staffed by physical therapists. Although not illustrated in the exemplary embodiment, a typical system 100 will have several balance testing centers 110 for every regional balance center 160, and the typical balance testing center 110 will be located remotely (i.e., at least two miles) from the nearest regional balance center 160.

The network 140 is preferably the global computer network commonly referred to as the "Internet." The network 140 is alternatively an intranet or other private network. The network 140 allows the separate steps of diagnostic testing and test result evaluation to be carried on at separate and remote locations, extending the reach of the expertise of the regional balance center 150.

A global patient database 150 is also linked with the network 140, providing remote access to patient data, including the patient's history, physical condition, and test results 152, the patient's insurance and billing data 154, and scheduling data 156. In this manner, the network 140 serves not only as a two-way channel of communication between the regional balance center 160 and the balance testing center 110, but also as a platform for accumulating, storing, and retrieving patient data. The global patient database 150 also provides empirical data from a large population of patients useful in studies evaluating various balance disorders, the accuracy of various diagnostic procedures, and the effectiveness of various therapies.

The balance testing center 110 has a plurality of balance disorder diagnostic tools, including a device 115 for testing hearing, a device 120 for testing vestibular ocular reflex, and a device 125 for testing the vestibular spinal reflex. Data from devices 115, 120, and 125 is conveyed to local computer database 130 via communication channels 117, 122, and 127. After the diagnostic data is collected by the local computer database 130, it is conveyed to the global patient database 150 or the regional balance center 160 via the network 140. In one embodiment, the local computer database 130 is a Microsoft Access database.

The network-based system 100 for diagnosing balance disorders also provides a patient 170 with access to the network 140 and portions of the global patient database 150. This access enables the patient to register and schedule an appointment for diagnostic testing from any computer hooked up to the network 140. The system 100 further provides primary care physicians (PCPs) and health administrators (e.g., health maintenance organization administrators, third party payers) with access to the network 140. This connection facilitates PCP authorization of balance diagnosis and therapy. It also facilitates communication regarding a patient's diagnostic test results and recommended therapy regimen from the regional balance center 160 to the patient's PCP 180.

FIG. 1, of course, is an exemplary embodiment of the present invention that incorporates many features not intended to be limiting. Numerous variations, enhancements, subtractions, and substitutions could be made to components of the system 100 without departing from several of the aspects of the present invention. For example, the global patient database 150 may reside at a regional balance center 160, or different kinds of patient information could be stored at different locations. Alternatively (or in addition), the regional balance center 160 may be substituted with an individual clinician qualified to evaluate vestibular balance data from any computer terminal connected to the network 140. Similarly, the balance testing center 110 may be replaced with a portable balance testing system. Also, the balance testing center 110 could employ different vestibular diagnostic tests, or transmit the results directly to the network 140 without first being collected and organized by a test data aggregator 130 such as a database. Furthermore, access could be denied altogether to patients 170 or primary care physicians 180 without sacrificing all of the aspects of the present invention.

Figure 2:
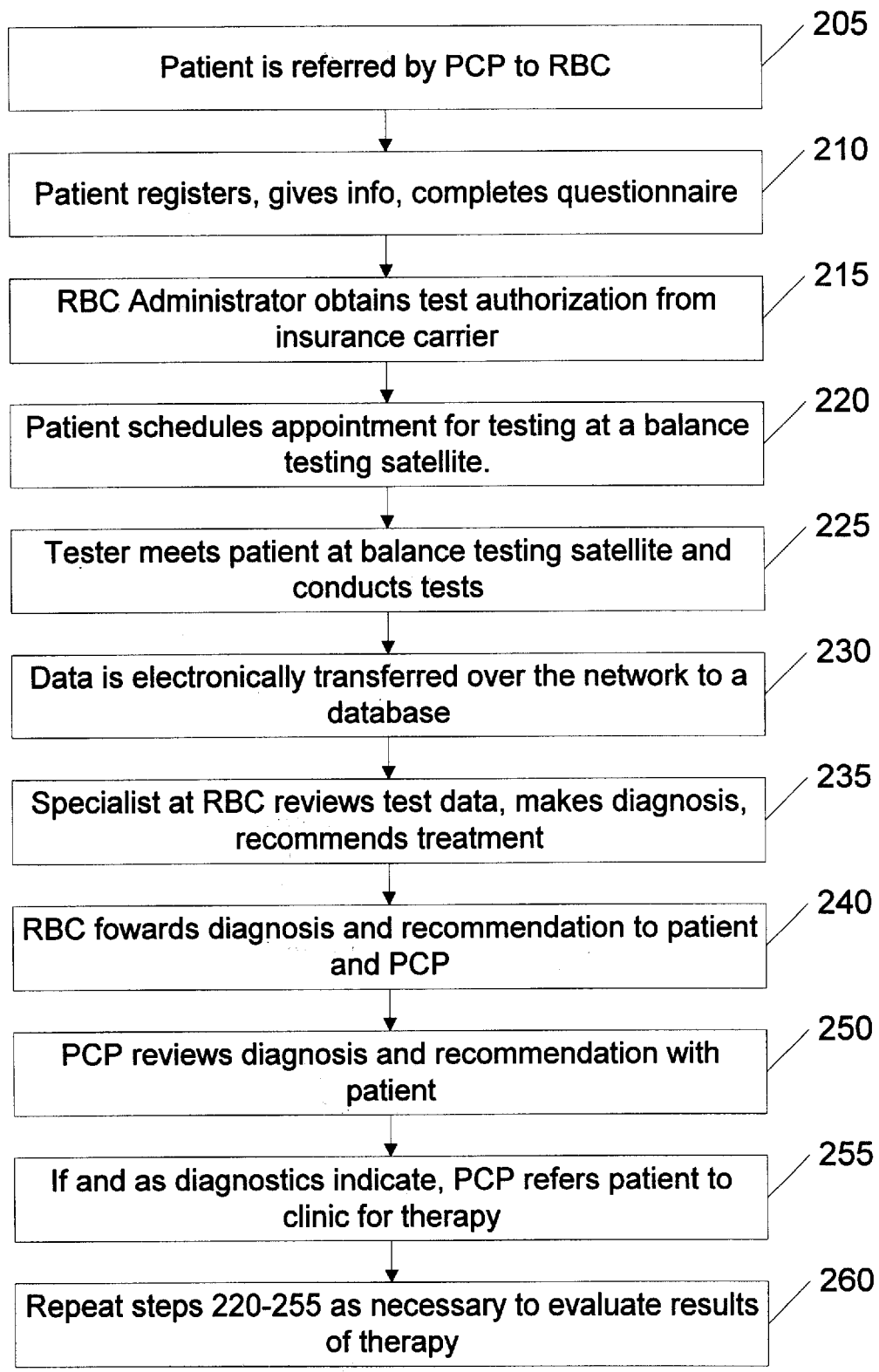
FIG. 2 is a functional flow diagram of one embodiment of a process of remotely scheduling and evaluating diagnostic tests for balance disorders.

FIG. 2 is a functional flow diagram of an embodiment of an advanced method for diagnosing balance disorders via a network. In step 205, a primary care physician refers a patient to a regional balance center. In step 210, the patient registers, provides personal and financial information, including insurance data, and completes a questionnaire. In the exemplary embodiment, the patient is given the opportunity to perform this step completely on-line. The patient is also given a choice to print out the necessary forms so that they can be sent in by regular mail.

In step 215, an administrator at the regional balance center obtains authorization from the patient's insurance carrier to conduct the diagnostic tests. In step 220, the patient schedules an appointment for testing at a balance center. In step 225, the patient goes to a satellite balance testing center to undergo a battery of vestibular diagnostic tests, which are administered by a suitable tester such as a physical trainer or trainer's assistant. In step 230, the data is transmitted electronically over a network to a database.

In step 235, a specialist at the regional balance clinic reviews the test data, makes a diagnosis, and recommends a treatment. In step 240, the specialist's diagnosis and recommendation are forwarded to the patient's primary care physician. In step 250, the primary care physician reviews the diagnosis and recommendation with the patient. In step 255, the primary care physician refers the patient to the clinic for therapy. In step 260, steps 220 through 255 are repeated as necessary to evaluate the results of the therapy.

Many of the steps can be rearranged or reordered without detracting from many of the aspects of the present invention.

For example, step 220 could be modified slightly and collapsed into step 210, so that the patient would make a provisional appointment for testing subject to authorization by the insurance carrier. Emails could be sent later to the patient to confirm or remind the patient of the reservation.

One enhancement of the embodiment of FIG. 2 would be to precede step 205 with step 210. In that case, a patient could electronically submit a request to his or her PCP for a referral, eliminating the need to independently seek the referral. Such an enhanced process, of course, would require acceptance by the patient's insurer.

While particular embodiments of the invention have been illustrated and described, it will be obvious to those skilled in the art that various changes and modifications may be made without sacrificing the advantages provided by the methods and apparatuses disclosed herein.

What we claim is:

1. A method of administering a medical practice to diagnose and treat balance disorders, comprising:

administering a plurality of diagnostic tests to produce diagnostic test data;

storing the diagnostic test data at a first data storage facility communicatively coupled to the Internet;

accessing the Internet to retrieve the diagnostic test data from the first data storage facility;

evaluating the diagnostic test data to detect and diagnose a balance disorder;

recommending a therapeutic regimen, if needed, to treat the balance disorder;

storing an electronic form of the recommended therapeutic regimen, if any, at the first data storage facility or a second data storage facility communicatively coupled to the Internet;

accessing the Internet to retrieve the recommended therapeutic regimen, if any; and implementing the recommended therapeutic regimen, if any.

2. The method of claim 1, wherein the diagnostic tests are administered using a portable balance testing system.

3. The method of claim 1, wherein the diagnostic tests are administered at a balance testing facility at a first location, and wherein the diagnostic test data is evaluated at a regional balance center at a second location remote from the first location.

4. The method of claim 1, further comprising providing a publicly accessible Internet site to permit a patient to register and schedule an appointment for diagnostic testing from an unspecified computer connected to the Internet.

5. The method of claim 4, further comprising providing the patient who accesses the publicly accessible Internet site to register and schedule an appointment with an online questionnaire.

6. The method of claim 5, where the questionnaire asks questions about the patient's physical condition and medical history.

7. The method of claim 5, where the questionnaire asks questions about any insurance coverage carried by the patient.

8. The method of claim 4, further comprising providing the patient with access to the recommended therapeutic regimen through the publicly accessible Internet site.

9. The method of claim 1, further comprising providing security to restrict access to persons authorized to review the diagnostic test data and recommended therapeutic regimen.

10. An integrated practice management system for diagnosing and treating balance disorders, comprising:

a plurality of balance testing satellites for administering tests to diagnose balance disorders and producing diagnostic test data;

a diagnostic center where the diagnostic test data is evaluated, a diagnosis is made, and a therapeutic regimen is recommended, the diagnostic center being located at a remote physical location from at least one of the balance testing satellites;

interfaces between each balance testing satellite and the Internet for transmitting the diagnostic test data; and an interface between the diagnostic center and Internet for receiving the diagnostic test data and for transmitting the diagnosis and recommended therapeutic regimen.

11. The integrated practice management system of claim 10, further comprising a publicly accessible Internet site to permit a patient to register and schedule an appointment for diagnostic testing from an unspecified computer connected to the Internet.

12. The integrated practice management system of claim 10, further comprising online means to permit a patient to register and schedule an appointment with an online questionnaire.

13. The integrated practice management system of claim 12, further comprising an online questionnaire asks questions about the patient's physical condition and medical history.

14. The integrated practice management system of claim 12, further comprising an online questionnaire asks questions about the patient's health insurance provider, if any.

15. The integrated practice management system of claim 10, further comprising means for tracking billing and payment for services provided to patients.

16. The integrated practice management system of claim 10, further comprising an interface between an office of a primary care physician and the Internet to provide access to the diagnosis and recommended therapeutic regimen.

17. A system for diagnosing balance function, the system comprising:

a test administration center at which a plurality of balance diagnostic tests are administered on a patient, said diagnostic tests producing diagnostic data;

a computer network that receives said diagnostic data from said test administration center;

a patient database that stores said diagnostic data from said test administration center;

a test evaluation center where said diagnostic data is retrieved from said patient database and evaluated by a skilled clinician to produce a diagnosis for said patient;

a communicative link, through said computer network, between said regional balance enter and a primary care physician of said patient, whereby said clinician can communicate said diagnosis to said primary care physician; and a communicative link, via said computer network, to said patient, whereby said patient can register and schedule to have said plurality of diagnostic tests administered to said patient.

18. The system of claim 17, wherein said plurality of balance diagnostic tests includes a vestibular spinal reflex test.

19. The system of claim 17, wherein said plurality of balance diagnostic tests includes a vestibular ocular reflex test that evaluates eye movements in response to head movements.

20. The system of claim 17, wherein said plurality of balance diagnostic tests includes a hearing analysis.

21. The system of claim 17, wherein said plurality of balance diagnostic tests includes a vestibular spinal reflex test and a vestibular ocular reflex test.

22. The system of claim 17, wherein said plurality of balance diagnostic tests includes a vestibular spinal reflex test, a vestibular ocular reflex test, and a hearing analysis.

23. A system for diagnosing the balance system of a patient, the system comprising:
- a vestibular ocular reflex test device that produces a first diagnostic data set;
- a vestibular spinal reflex test device that produces a second diagnostic data set, said vestibular spinal reflex test device located in close proximity to said vestibular ocular reflex test device; and
- a computer network communicatively coupling said vestibular ocular reflex test device and said vestibular spinal reflex test device with a test evaluation center located at least two miles away from said vestibular ocular reflex test device, the computer network enabling a skilled clinician at said test evaluation center to evaluate both said first and said second diagnostic data sets.

24. The system of claim 23, further comprising a patient database communicatively coupled with said computer network, the database storing said first and second diagnostic data sets.

25. The system of claim 23, further comprising a local computer database located proximate to said vestibular ocular reflex tester and said vestibular spinal reflex tester and communicatively coupled therewith, said database storing and communicating said first and second diagnostic data sets to said computer network.

26. The system of claim 24, wherein said patient database comprises patient condition data, patient history data, patient test data, patient insurance data, patient billing data, and scheduling data, which the patient, a healthcare provider or an office administrator can access from the computer network.

27. A process for diagnosing the balance system of a patient, the process comprising:
- the patient scheduling an appointment for a plurality of diagnostic balance tests;
- administering, at the appointed time, the plurality of diagnostic balance tests on the patient using diagnostic testing machines that generate diagnostic data, said plurality of diagnostic balance tests being administered at a first location;
- transmitting the diagnostic data from said diagnostic testing machines to a patient database that stores said diagnostic data;
- retrieving, at a second location distinct and independent from the first location, the diagnostic data from said patient database; and
- evaluating the diagnostic data to diagnose the patient.

28. The process of claim 27, wherein the patient uses a computer connected to a computer network to register, schedule, and verify insurance coverage for the appointment.

29. The process of claim 27, further comprising recommending therapy to improve the patient's vestibular functioning.

30. The process of claim 29, further comprising forwarding the diagnosis and recommended therapy to a primary care physician of the patient.

31. The process of claim 27, further comprising a primary care physician referring the patient to a physical therapy clinic for therapy.

32. The process of claim 27, further comprising obtaining authorization from an insurance carrier of the patient to administer the diagnostic balance tests.

33. The process of claim 27, further comprising a primary care physician referring the patient to a provider of the diagnostic balance tests.

34. The process of claim 33, further comprising:
- the patient registering and scheduling with the provider and completing a questionnaire for the provider;
- obtaining authorization from an insurance carrier of the patient to administer the diagnostic balance tests;
- reading the diagnostics and providing a consult letter on the recommended treatment plan to improve the patient's vestibular functioning;
- forwarding the diagnosis and the recommended treatment plan to the primary care physician and the patient; and
- the primary care physician referring the patient to the clinic for therapy when deemed appropriate.

* * * * *